United States Patent [19]
Brown

[11] Patent Number: 5,329,541
[45] Date of Patent: Jul. 12, 1994

[54] LASER CONNECTOR CONVERSION ADAPTOR

[75] Inventor: Joseph D. Brown, Acworth, Ga.

[73] Assignee: CeramOptec, Inc., Enfield, Conn.

[21] Appl. No.: 881,358

[22] Filed: May 11, 1992

[51] Int. Cl.⁵ .......................... G02B 6/32; H01S 3/097
[52] U.S. Cl. ........................................ 372/88; 385/88
[58] Field of Search .................... 385/88-92; 372/88

[56] References Cited

U.S. PATENT DOCUMENTS 3,618,526 11/1971 Baker ............................... 372/77 X
5,108,167 4/1992 Kandpal et al. ...................... 385/33
5,163,114 11/1992 Hendow ................................. 385/88

*Primary Examiner*—Akm E. Ullah
*Attorney, Agent, or Firm*—Kenneth P. Glynn

[57] ABSTRACT

The present invention is directed to an adaptor for the conversion of laser connectors which will render a pre-existing laser system having an inside connector receptive to and connectable to an otherwise non-fitting generic or proprietary outside connector. This adaptor includes a locking sleeve and a captive sleeve located within the locking sleeve. The captive sleeve comprises of a pigtail attachment and a pre-existing laser system outside connector. The pigtail attachment has a forward end and a rearward end and is adapted to connect to a pre-existing laser system outside connector with extended fiber at its forward end and is adapted with connecting means for receiving a final outside connector different from the pre-existing laser system outside connector, at its rearward end. The pigtail attachment has locking means with a first position and a second position.

18 Claims, 4 Drawing Sheets

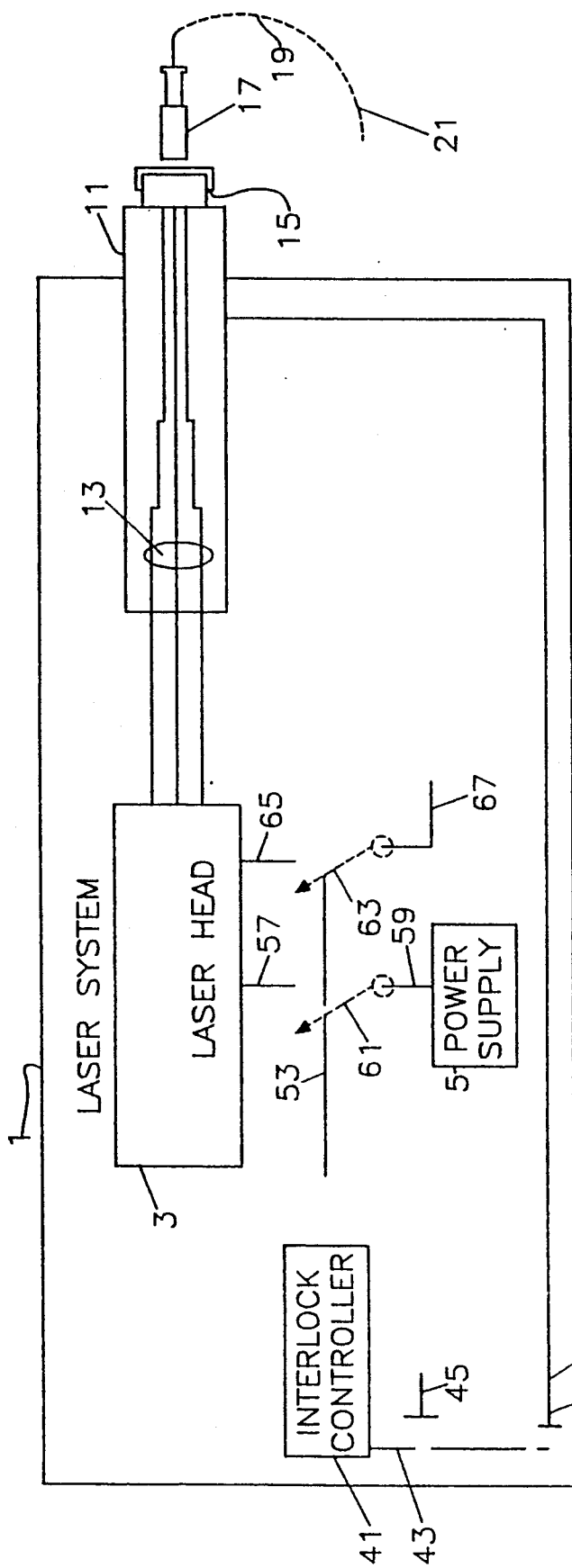
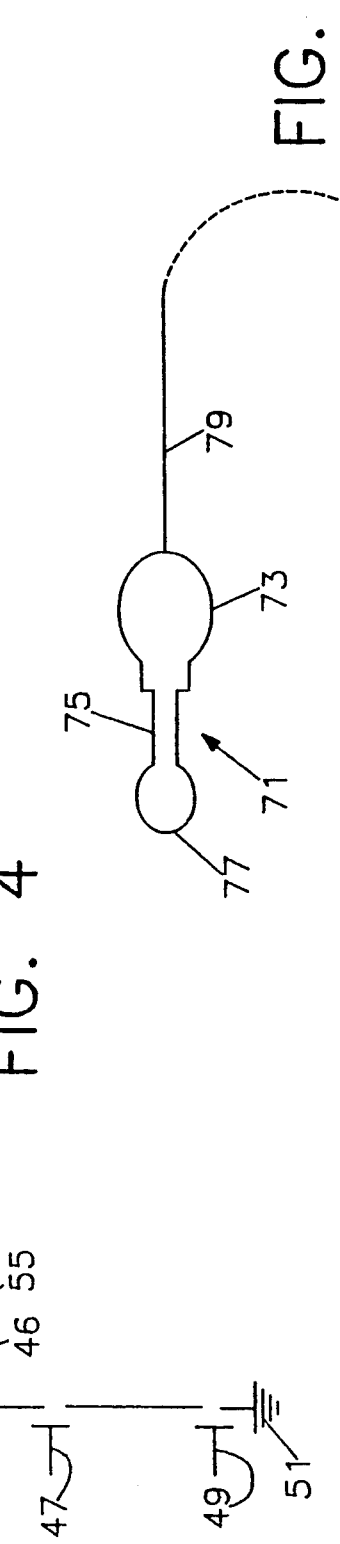
FIG. 4
FIG. 5

LASER CONNECTOR CONVERSION ADAPTOR

BACKGROUND OF THE INVENTION

1. Field of the Invention

The present invention relates to a device for converting laser systems with custom or proprietary accessory connectors to a new type of generic connector. The invention is particularly advantageous for surgical laser systems having various interlock features.

2. Prior Art Statement

Many laser companies have made their own custom or proprietary connectors for output of laser systems to optical fibers. Such connectors only allow for attachment of accessories with the complementary connectors so as to preclude competition from selling accessories to owners or users of such laser systems. The laser manufacturer attempts to insure that the customers only buy their optical fiber attachments and accessories.

Prior to the present invention, the typical laser system would have an adaptor which would include the condensing lens as well as either the male or female proprietary connector. The optical fiber device or other accessory would have the counterpart, i.e. the female or male connector. Conversion to a different connector would require the removal of the existing adaptor and the substitution of a new adaptor in its place with the appropriate connector to receive substitute accessories and attachments which would have the proprietary or custom connectors of the manufacturer providing the adaptor. In other words, in order for a competitor to sell its accessories and optical fibers to someone owning or using an existing laser system with a proprietary connector arrangement, the adaptor had to be removed and replaced with a new adaptor to fit the new line of products.

It is an object of the present invention to provide for a laser connector conversion adaptor which would allow interchangability of various proprietary and non-proprietary connectors with adaptors and pre-existing laser systems having proprietary connectors without the need to remove and replace the existing adaptor containing the condensing lens and the connector.

SUMMARY OF THE INVENTION

The present invention is directed to an adaptor for the conversion of laser connectors which will render a pre-existing laser system having an inside connector receptive to and connectable to an otherwise non-fitting generic or proprietary outside connector. This adaptor includes a locking sleeve and a captive sleeve located at least partially within the locking sleeve. The captive sleeve comprises a pigtail attachment and a pre-existing laser system outside connector. The pigtail attachment has a forward end and a rearward end and is adapted to connect to a pre-existing laser system outside connector with extended fiber at its forward end and is adapted with connecting means for receiving a final outside connector different from the pre-existing laser system outside connector, at its rearward end. The pigtail attachment has locking means with a first position and a second position. The first position is such that the captive sleeve is not removable from the locking sleeve to the extent necessary to connect the outside connector and has a second position which does permit the removal or movement of captive sleeve sufficiently to permit the connection of the outside connecter. A preferred locking means is a lock collar secured to the pigtail attachment with a first position where a locking ring radially encloses the collar which prevents axial movement of the captive sleeve. In the second position, the locking ring radially increases so that the captive sleeve is free enough to allow the outside connector at the forward end to be connected to a laser system. This can only be done when the final outside connector is attached to the rearward end of the captive sleeve and the locking means is in its second position.

BRIEF DESCRIPTION OF THE DRAWINGS

The present invention will be more fully understood when the specification herein is taken in conjunction with the attached drawings wherein:

FIG. 4 shows a schematic diagram of more detail within a conventional laser system to show the complexity of the safety interlocking mechanisms;

FIG. 5 shows a side view of a typical proprietary outside connector;

DETAILED DESCRIPTION OF THE INVENTION AND DRAWINGS

Many laser system manufacturers today design systems with proprietary or customary output connectors. These permit for the interchangability of various attachments to the laser system by using only that manufacturer's complementary proprietary connectors.

Figure 1:
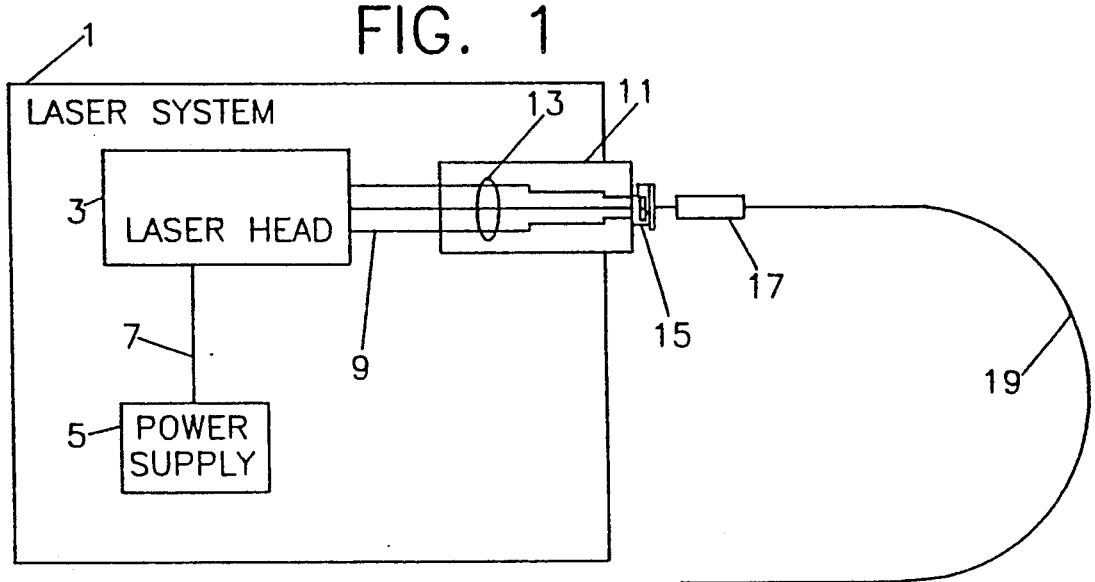
FIG. 1 shows a schematic diagram of a typical prior art laser system with proprietary connectors.

FIG. 1 shows a schematic diagram of a typical or conventional laser system 1. Included generally is laser head 3 with power supply 5 and connecting wiring 7. The laser output is shown as output 9 and adaptor 11 includes a condensing lens 13 as well as a proprietary connector 15. For purposes of simplicity in this application, the term "inside" and "outside" are used respectively to mean connectors which are attached to the laser system (inside) and connectors which are separate from the laser system and are attached to an accessory (outside).

Also shown in FIG. 1 is outside proprietary connector 17, optical fiber 19 and distal optical fiber end 21. This represents a typical accessory to a laser system such as laser system 1.

In all of the figures, the schematic diagram of the laser system and the other components are simplified and it is understood that the details and functioning of a typical laser system is a matter of ordinary skill as such systems are broadly commercially available. Further, the word "proprietary" is taken to mean custom-made or tailored to be different from generic.

Figure 2:
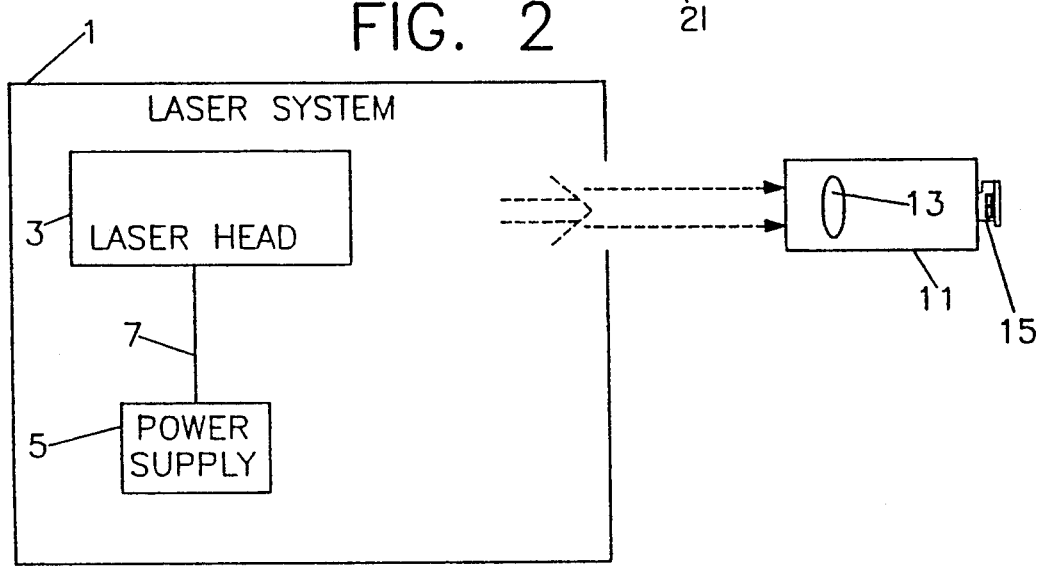
FIG. 2 shows the prior art laser system of FIG. 1 with the adaptor containing the inside proprietary connector being removed.
Figure 3:
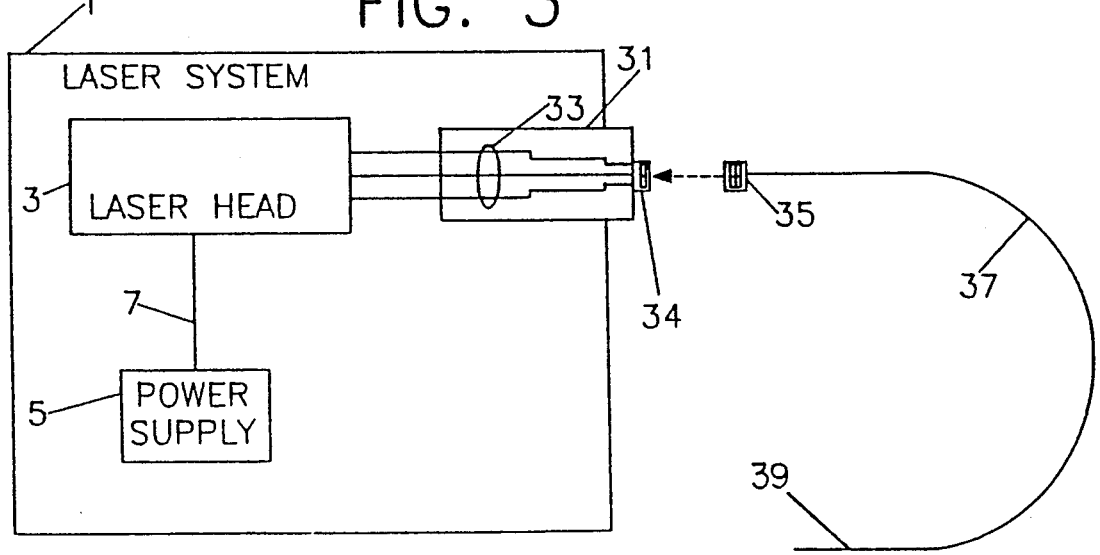
FIG. 3 shows a schematic diagram of a prior art laser system with a new adaptor and inside connector to receive an alternative proprietary or generic connector.

Referring to FIGS. 2 and 3, where parts identical to those set forth in FIG. 1 are identically numbered and need not be repeated, it is shown that the adaptor 11 containing inside proprietary connector 15 and lens 13 is required to be removed in order to enable other types of outside connectors to be attached thereto. Thus, as shown in FIG. 3, a replacement adaptor 31 is retrofitted into the laser system, containing a condensing lens 33 and inside connector 34. By utilizing the substitute adaptor 31, a different type of inside connector 34 is utilized and thus alternative accessories such as that containing outside connector 35, optical fiber 37 and distal optical fiber end 39. It might be the case that inside connector 34 and outside connector 35 are conventional type of generic connectors or may be proprietary connectors but different from those of the original laser manufacturer.

FIG. 4 shows laser system 1 in more detail and, again, like parts are like numbered. However, here, while FIGS. 1 through 3 show the general concept of a laser system, FIG. 4 shows some of the important features with respect to the interlock safety features of laser systems as required by the Food and Drug Administration of the United States Government. The safety interlock of the laser system is to basically insure that the laser system does not operate when an optical fiber is not properly connected. Hopefully, the safety feature minimizes the chance of accidental laser exposure to the patient or operating personnel or others who may be in the area of the laser when it is running. FIG. 4 shows interlock controller 41 with connecting wire 43 which may be closed or opened with laser key switch 45 and separately may be closed or opened via fiber connect switch 46. Fiber connect switch 46 is connected via a feedback line 55 to adaptor 11 and can only be completed when outside connector 17 is properly connected to inside connector 15. Further, a remote door switch 47 is included so that the system cannot be operated unless the door is appropriately closed. Finally, a foot switch 49 and ground 51 are essential to the proper functioning. Power supply 5 is wired with lines 57 and 59 to the laser head and lines 65 and 67 to the shutter and have interlock switches which are normally open when one of the interlock switches is opened. Thus switches 61 and 63 will respond to the interlock controller which will itself be a function of the condition of the various switches involved in the interlock system. Thus, unless all of the interlock switches in the series of the chain are closed, the laser operation cannot occur due to shutters and an interrupted power supply. For this reason, it is important that any adaptor exchanges must still provide and indication to the chain as to whether or not a fiber is properly installed, in order to prevent accidental exposures.

In summary, adaptors which replace the inside connectors must provide for a method to convert from the existing laser system proprietary connector to a nonproprietary or alternative proprietary connector without sacrificing the functionality or reliability of the interlock system.

The present invention is directed to a novel adaptor and adaptor system which will enable one to take a pre-existing laser system with pre-existing inside connectors and outside connectors and to modify that system and those connectors such that generic outside connector type accessories may be attached to the otherwise proprietary laser system itself. This is done without the removal of the main adaptor containing the condensing lens and the inside connector and without the need to wire or rewire with respect to the interlocked controller. In fact, a very substantial advantage of the present invention relates to the fact that the conversion is achieved without any tampering, altering or removal of the main laser system itself, including the inside connector and related mechanisms. Further, the present invention advantageously utilizes whatever outside proprietary connector would have normally been used with the proprietary laser system. This not only reduces the cost, but enables a single accessorized laser system with proprietary connectors to be converted with a single adaptor and adaptor system so as to receive a plurality of different accessories using generic final outside connectors.

FIG. 5 shows a side view of a typical detailed "bare bones" proprietary male connector which is used as an example of the connector which will be contained within the present invention system. Thus, in FIG. 5, male proprietary connector 71 includes locking head 77, elongated insertion member 75 and fiber lock mechanism 73. Optical fiber 79 extends from fiber lock mechanism 73 for locking optical fiber 79 into the connector.

Figure 6A:
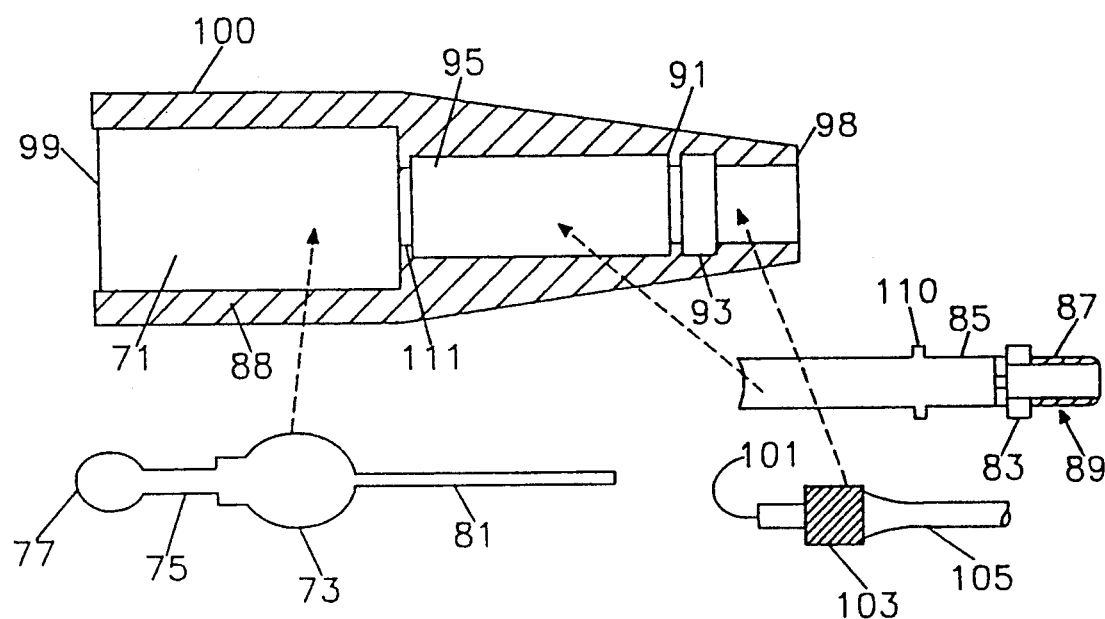
FIGS. 6(a) and (b) shows a side cut view of a present invention laser connection conversion adaptor and system with locking means in its first position.
Figure 6B:
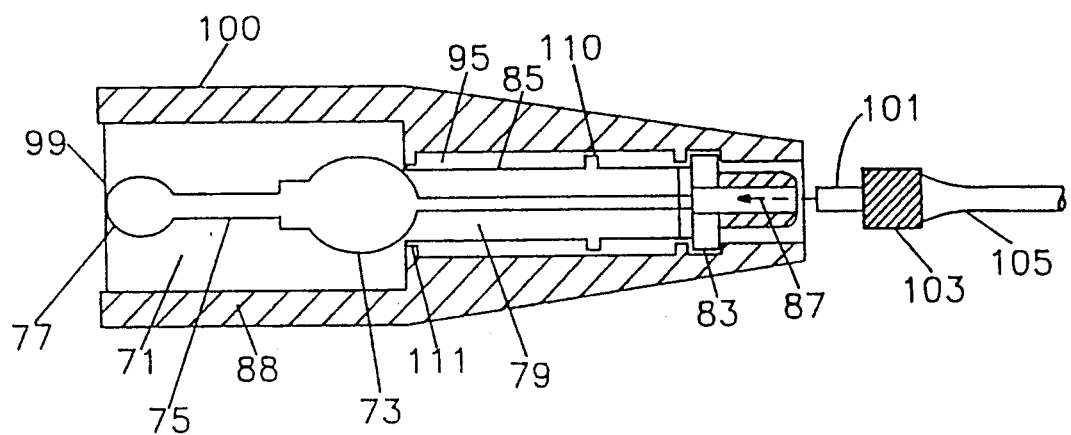

FIG. 6a, illustrates the major components of present invention adaptor 100. Referring now to FIGS. 6a, 6b, 7 and 8, there is shown respectively present invention adaptor 100 in its locked position, in its released position with only the final outside connector attached, and in its extended position with both the final outside connecter attached and the original outside connecter being attached to the proprietary laser system.

Referring again to FIG. 6b, there is shown adaptor 100 which includes locking sleeve 88 having a system end 99 and a rearward end 98, as well as captive sleeve assembly 89 comprising of a pigtail arrangement 85 and a pre-existing laser system proprietary outer connector.

Pigtail arrangement 85 has a forward end with a clamping of optical fiber 79 which extends from fiber lock mechanism 73 of the pre-existing laser system proprietary outer connector 71. Further, pigtail arrangement 85 includes connecting means for connection to final outer connector 103. Here the connecting means are threads 87, although snap-in or any other type of connecting means could be used without exceeding the scope of the invention. Likewise, final outer connector 103 has threads contained therein to thread onto threads 87, but could include any alternative connecting means to correspond to such alternative connecting means of pigtail arrangement 85.

Final outer connector 103 includes optical fiber end 101 and an optional fiber housing 105, as shown. Pigtail arrangement 85 includes one or more locking means such as lock collar 83. The lock collar 83 in the first position is radially perpendicular to a smaller radius locking ring 91 and nests in recess 93. Note that smaller radius locking ring prevent axial movement captive sleeve assembly 89. If one were to simply push on the rearward end of pigtail arrangement 85 in a direction into locking sleeve 88, it can be seen that movement would stop at the end of the lock ring 91 opening and further movement would be prevented.

Figure 7:
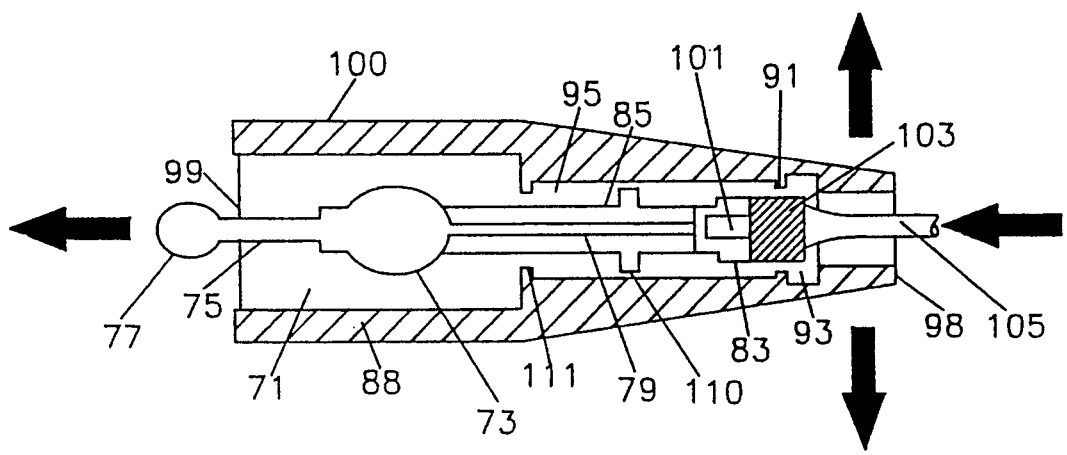
FIG. 7 shows a side cut view of the present invention device shown in FIG. 6 but with the final outside connecter being connected to the pigtail attachment and with the locking means in its second position; and, FIG. 8 shows a side cut view of the present invention device shown in FIGS. 6 and 7 but now fully connected to a pre-existing laser system with a proprietary connector arrangement.

Referring now to FIG. 7, it should be noted that final outer connector 103 has been screwed on to threads 87 of pigtail arrangement 85 and, in so doing, the locking sleeve end 98 would move radially outward relative to pigtail arrangement 85, thereby moving locking means outward so as to no longer inhibit the lock collar 83 at the captive sleeve. Thus, the now connected final outer connector 103, along with captive sleeve 89, containing the pigtail arrangement 85, and the pigtailed fiber 83, fiber 79 and outer connector 71 is moved forward as shown by the arrows. Thus, movement is now permitted within adaptor 100 to permit outer connector 71 to be connected to a laser system. Also note that maximum axial travel of the captive sleeve assembly is controlled by a mechanical stop 110 on the pigtail arrangement and the mechanical stop 111 on the locking sleeve.

Figure 8:
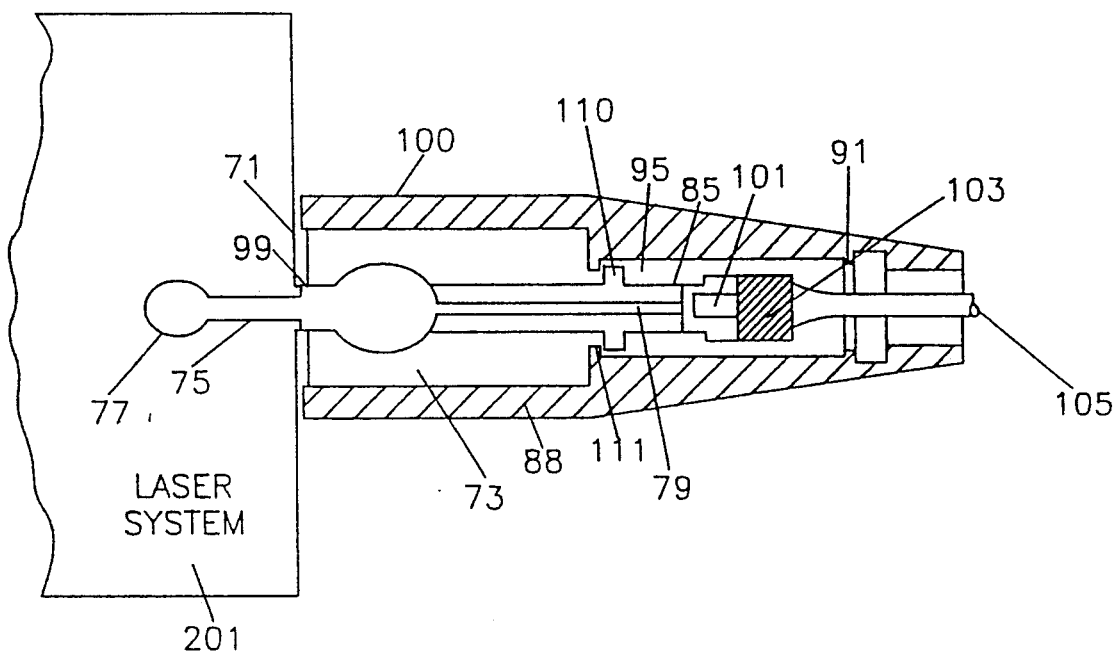

As seen in FIG. 8, adaptor 100 and outer connector 71 have now been connected to the pre-existing laser system 201 which, as mentioned above, has its conventional inner connector (not shown). By conventional inner connector is meant the original proprietary inner connector that did not require any modification in order to effect the generic or proprietary final outer connector arrangement set forth in the adaptor system described herein. Variations on the present invention as set forth above should now be seen by the artisan and the present invention should not be construed as being limited to the specific examples which are set forth merely to illustrate but not to limit the invention. For example, the locking means may be springs, pins, spring-loaded balls, sockets, mechanisms that are pinched or squeezed and passed through the locking sleeve so that depression is required for connection. However, it is believed that the embodiment shown in FIGS. 6a through 8 is a preferred embodiment of the present invention. Further, as mentioned, the connecting means at the end of pigtail arrangement 85 could be other than threaded, and any conventional connecting means therein is useful. In addition, various springs, guides, rings, stops and other mechanisms could be included to stabilize, secure, bias or otherwise enhance the functionality of the present invention adaptor, without exceeding the scope of the present invention.

What is claimed is:

1. A laser connector conversion adaptor system for rendering a pre-existing laser system inside connector receptive to and connectable to an otherwise non-fitting, incompatible outside connector, which comprises:
   (a) a locking sleeve having a system end for connection to an inside connector and a rearward end for connection to an outside connector which is a non-fitting and incompatible with said inside connector; and,
   (b) a captive sleeve assembly located at least partially within said locking sleeve, including a pigtail attachment having a forward end and a rearward end, said forward end of said pigtail attachment being adapted to connect to a pre-existing laser system outside connector with extended fiber by attachment to said forward end of said pigtail attachment to said extended fiber, said pigtail attachment having a connective means for receiving a final outside connector for attachment to and compatible with an inside connector, said pigtail attachment having locking means with a first position and a second position within said locking sleeve and within said captive sleeve such that when said locking means is in said first position, the pigtail attachment is not removable from said locking sleeve to connect to an outside connector, and also such that when said locking means is in said first position said final outside connector is not connected to said connective means of said pigtail attachment, and when said locking means is in said second position within said locking sleeve and within said captive sleeve, said final connector is connected to said connective means of said pigtail attachment and said pigtail attachment is removable from said locking sleeve sufficiently to connect said final outside connector to an inside connector of a laser system.

2. The adaptor of claim 1, wherein said locking means is at least one locking sleeve which has a locking position with a reduced radius perpendicular to said pigtail attachment for its first position and an unlocking position with an increased radius perpendicular to said pigtail attachment for its second position.

3. The adaptor of claim 2, wherein said locking sleeve is tubular and of a predetermined diameter and has a central inner diameter greater than said predetermined diameter, said central inner diameter area being adapted to cooperate with said locking sleeve in its first position.

4. The adaptor of claim 1, wherein said captive sleeve assembly is biased within said locking sleeve in the direction of the rear end of said pigtail attachment when said locking means is in its first position.

5. The adaptor of claim 4, wherein said bias is achieved by a spring bias.

6. The adaptor of claim 1, wherein said locking sleeve is slidable over said captive sleeve attachment to move said locking means from its first position to its second position.

7. An adaptor for conversion of proprietary connectors of laser systems to non-proprietary connection capabilities, which comprises:
   (a) a hollow locking sleeve of a predetermined length, cross-section and thickness, having a general predetermined inner diameter and a central inner diameter greater than said predetermined inner diameter;
   (b) a captive sleeve located at least partially within said locking sleeve; and,
   (c) a pigtail attachment for receiving an outside proprietary connector and fiber, being at least partially within said captive sleeve, and adapted to receive a final connector, said pigtail attachment having a locking means with a first position to prevent an outside proprietary connector from being connected to a laser system, and a second position to permit an outside proprietary connector to be connected to a laser system, wherein said locking means is at least one lock ring which has a locking position with a decreased radius perpendicular to said pigtail attachment for its first position and an unlocking position with an increased radius perpendicular to said pigtail attachment for its second position.

8. The adaptor of claim 7, wherein said locking sleeve is tubular and of a predetermined diameter and has a central inner diameter greater than said predetermined diameter, said central inner diameter area being adapted to cooperate with said lock collar in its first position.

9. The adaptor of claim 7, wherein said captive sleeve is biased within said locking sleeve in the direction of the rear end of said pigtail attachment when said locking means is in its first position.

10. The adaptor of claim 9, wherein said bias is achieved by a spring bias.

11. A laser connector conversion adaptor system for rendering a pre-existing laser system inside connector receptive to and connectable to an otherwise non-fitting outside connector, which comprises:

(a) a locking sleeve;
(b) a captive sleeve located at least partially within said locking sleeve, including a pigtail attachment having a forward end and a rearward end, and being adapted to connect a pre-existing laser system outside connector with extended fiber, by attachment of said forward end of said pigtail attachment to said extended fiber, said pigtail attachment having a connective means for receiving a final outside connector for attachment to and compatible with an inside connector, said pigtail attachment having locking means with a first position within said locking sleeve such that the captive sleeve is not removable from said locking sleeve to connect said inside connector, and said locking means is in said first position when said final connector is not connected to said connective means of said pigtail attachment, and said locking means having a second position within said locking sleeve such that the captive sleeve is removable from said locking sleeve sufficiently to connect said inside connector to a laser system, and said locking means is in said second position when said final connector is connected to said connective means of said pigtail attachment;
(c) a pre-existing laser system outside connector with extended fiber attached to the forward end of said pigtail attachment; and,
(d) a final outside connector adapted to attach to said rearward end of said pigtail attachment.

12. The adaptor system of claim 11, wherein said locking means is at least one radial lock ring which has a locking position perpendicular to said pigtail attachment for its first position and an unlocking position with an increase locking radius perpendicular to said pigtail attachment for its second position.

13. The adaptor system of claim 12, wherein said captive sleeve is tubular and of a predetermined diameter and has a central inner diameter greater than said predetermined diameter, said central inner diameter with lock collar area being adapted to cooperate with said lock ring in its first position.

14. The adapter system of claim 11, wherein said captive sleeve is biased within said locking sleeve in the direction of the rear end of said pigtail attachment when said locking means is in its first position.

15. The adaptor system of claim 14, wherein said bias is achieved by a spring bias.

16. The adaptor system of claim 11, wherein said locking sleeve is slidable over said captive sleeve to move said locking means from its first position to its second position.

17. The adaptor system of claim 11, wherein said final outside connector and said rearward end of said pigtail attachment are threaded.

18. The adaptor system of claim 17, wherein said final outside connector is adapted to expand radially said captive sleeve and to move said locking means from said first position to its second position when said final outside connector is attached to said pigtail attachment.

* * * * *